(12) United States Patent
Matsuyama et al.

(10) Patent No.: US 6,699,695 B1
(45) Date of Patent: Mar. 2, 2004

(54) RHODOCOCCUS MICROORGANISMS AND PROCESS FOR PRODUCING AMIDE COMPOUNDS

(75) Inventors: Akinobu Matsuyama, Tsukuba (JP); Masato Kawabe, Otake (JP); Toru Nagasawa, Gifu (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/622,201

(22) PCT Filed: Dec. 13, 1999

(86) PCT No.: PCT/JP99/06994

§ 371 (c)(1),
(2), (4) Date: Aug. 14, 2000

(87) PCT Pub. No.: WO00/36086

PCT Pub. Date: Jun. 22, 2000

(30) Foreign Application Priority Data

Dec. 15, 1998 (JP) ............................................. 10/356229

(51) Int. Cl.⁷ ............................. C12P 13/02; C12N 1/20
(52) U.S. Cl. ................. 435/129; 435/252.1; 435/253.2; 435/822; 435/169
(58) Field of Search ............................. 435/129, 252.1, 435/253.2, 822, 169

(56) References Cited

U.S. PATENT DOCUMENTS 5,866,379 A * 2/1999 Burlingame et al. ........ 435/129
6,132,985 A * 10/2000 Pierce ........................ 435/129

FOREIGN PATENT DOCUMENTS

| EP | A2445646 | 9/1991 |
|---|---|---|
| EP | A2528669 | 2/1993 |
| EP | A2713914 | 6/1996 |
| JP | B2-5617918 | 4/1981 |
| JP | B2-5937951 | 9/1984 |
| JP | B2-6221519 | 5/1987 |
| JP | A6486889 | 3/1989 |
| JP | A2154692 | 6/1990 |
| JP | A440899 | 2/1992 |
| JP | A515384 | 1/1993 |
| JP | A530983 | 2/1993 |
| JP | A5236977 | 9/1993 |
| JP | A614786 | 1/1994 |
| WO | A1-9832872 | 7/1998 |

OTHER PUBLICATIONS

P. Juteau et al., "Analysis of the relative abundance of different types of bacteria capable of toluene degradation in a compost biofilter", Appl. Microbiol Biotechnol, vol 52, pp. 863–868, 1999.

Rainey et al., Microbiology vol. 141, No. 2, pp. 523–528 (1995).

* cited by examiner

Primary Examiner—Irene Marx
(74) Attorney, Agent, or Firm—Birch Stewart Kolasch & Birch LLP

(57) ABSTRACT

A nitrile compound having a complicated structure (e.g., 2-hydroxy-4-methylthiobutyronitrile) is converted into an amide compound with high production efficiency, by using a novel microorganism of which the gene 16S rRNA has a specific base sequence. As the microorganism, Rhodococcus sp. Cr4 strain and Rhodococcus sp. Am8 strain or the like is employed.

10 Claims, 1 Drawing Sheet

SEQUENCE LISTING

<160> NUMBER OF SEQ ID NOS: 2

<210> SEQ ID NO 1
<211> LENGTH: 1480
<212> TYPE: DNA

<213> ORGANISM: Unknown Organism
<220> FEATURE:
<223> OTHER INFORMATION: Description of Unknown Organism:16S rRNA gene
    of Rhodococcus sp. Cr4 (FERM BP-6596)

<400> SEQUENCE: 1

| | | | | | |
|---|---|---|---|---|---|
| cctggctcag | gacgaacgct | ggcggcgtgc | ttaacacatg | caagtcgaac | gatgaagccc | 60 |
| agcttgctgg | gtggattagt | ggcgaacggg | tgagtaacac | gtgggtgatc | tgccctgcac | 120 |
| ttcgggataa | gcccgggaaa | ctgggtctaa | taccggatat | gaccatgagc | tgcatggctc | 180 |
| gtggtggaaa | ggtttactgg | tgcaggatga | gcccgcggcc | tatcagcttg | ttggtggggt | 240 |
| aatggcctac | caaggcgacg | acgggtagcc | ggcctgagag | ggcgaccggc | cacactggga | 300 |
| ctgagacacg | gcccagactc | ctacgggagg | cagcagtggg | gaatattgca | caatgggcga | 360 |
| aagcctgatg | cagcgacgcc | gcgtgaggga | tgacggcctt | cgggttgtaa | acctctttca | 420 |
| gcagggacga | agcgcaagtg | acggtacctg | cagaagaagc | accggccaac | tacgtgccag | 480 |
| cagccgcggt | aatacgtagg | gtgcgagcgt | tgtccggaat | tactgggcgt | aaagagctcg | 540 |
| taggcggttt | gtcgcgtcgt | ctgtgaaaac | ccgcagctca | actgcgggct | tgcaggcgat | 600 |
| acggcagac | ttgagtactg | caggggagac | tggaattcct | ggtgtagcgg | tgaaatgcgc | 660 |
| agatatcagg | aggaacaccg | gtggcgaagg | cgggtctctg | gcagtaact | gacgctgagg | 720 |
| agcgaaagcg | tgggtagcga | acaggattag | ataccctggt | agtccacgcc | gtaaacggtg | 780 |
| ggcgctaggt | gtgggtttcc | ttccacggga | tccgtgccgt | agctaacgca | ttaagcgccc | 840 |
| cgcctgggga | gtacggccgc | aaggctaaaa | ctcaaaggaa | ttgacggggg | cccgcacaag | 900 |
| cggcggagca | tgtggattaa | ttcgatgcaa | cgcgaagaac | cttacctggg | tttgacatat | 960 |
| accggatcgc | ctcagagatg | gggtttccct | tgtggtcggt | atacaggtgg | tgcatggctg | 1020 |
| tcgtcagctc | gtgtcgtgag | atgttgggtt | aagtcccgca | acgagcgcaa | cccttgtcct | 1080 |
| gtgttgccag | cacgtaatgt | tggggactcg | caggagactg | ccggggtcaa | ctcggaggaa | 1140 |
| ggtggggacg | acgtcaagtc | atcatgcccc | ttatgtccag | ggcttcacac | atgctacaat | 1200 |
| ggccggtaca | gagggctgcg | ataccgtgag | gtggagcgaa | tcccttaaag | ccggtctcag | 1260 |
| ttcggatcgg | ggtctgcaac | tcgaccccgt | gaagtcggag | tcgctagtaa | tcgcagatca | 1320 |
| gcaacgctgc | ggtgaatacg | ttcccgggcc | ttgtacacac | cgcccgtcac | gtcatgaaag | 1380 |
| tcggtaacac | ccgaagccgg | tggcctaacc | ccttgtggga | gggagccgtc | gaaggtggga | 1440 |
| tcggcgattg | ggacgaagtc | gtaacaaggt | agccgtaccg | | | 1480 |

<210> SEQ ID NO 2
<211> LENGTH: 1480
<212> TYPE: DNA
<213> ORGANISM: Unknown Organism
<220> FEATURE:
<223> OTHER INFORMATION: Description of Unknown Organism:16S rRNA gene
    of Rhodococcus sp. Am8 (FERM BP-6595)

<400> SEQUENCE: 2

| | | | | | |
|---|---|---|---|---|---|
| cctggctcag | gacgaacgct | ggcggcgtgc | ttaacacatg | caagtcgaac | gatgaagccc | 60 |
| agcttgctgg | gtggattagt | ggcgaacggg | tgagtaacac | gtgggtgatc | tgccctgcac | 120 |
| ttcgggataa | gcccgggaaa | ctgggtctaa | taccggatat | gaccatgagc | tgcatggctc | 180 |
| gtggtggaaa | ggtttactgg | tgcaggatga | gcccgcggcc | tatcagcttg | ttggtggggt | 240 |
| aatggcctac | caaggcgacg | acgggtagcc | ggcctgagag | ggcgaccggc | cacactggga | 300 |
| ctgagacacg | gcccagactc | ctacgggagg | cagcagtggg | gaatattgca | caatgggcga | 360 |

-continued

```
aagcctgatg cagcgacgcc gcgtgaggga tgacggcctt cgggttgtaa acctctttca      420
gcagggacga agcgcaagtg acggtacctg cagaagaagc accggccaac tacgtgccag      480
cagccgcggt aatacgtagg gtgcgagcgt tgtccggaat tactgggcgt aaagagctcg      540
taggcggttt gtcgcgtcgt ctgtgaaaac ccgcagctca actgcgggct tgcaggcgat      600
acgggcagac ttgagtactg caggggagac tggaattcct ggtgtagcgg tgaaatgcgc      660
agatatcagg aggaacaccg gtggcgaagg cgggtctctg ggcagtaact gacgctgagg      720
agcgaaagcg tgggtagcga acaggattag ataccctggt agtccacgcc gtaaacggtg      780
ggcgctaggt gtgggtttcc ttccacggga tccgtgccgt agctaacgca ttaagcgccc      840
cgcctgggga gtacggccgc aaggctaaaa ctcaaaggaa ttgacggggg cccgcacaag      900
cggcggagca tgtggattaa ttcgatgcaa cgcgaagaac cttacctggg tttgacatat      960
accggatcgc ctcagagatg gggtttccct tgtggtcggt atacaggtgg tgcatggctg     1020
tcgtcagctc gtgtcgtgag atgttgggtt aagtcccgca acgagcgcaa cccttgtcct     1080
gtgttgccag cacgtaatgt tggggactcg caggagactg ccggggtcaa ctcggaggaa     1140
ggtggggacg acgtcaagtc atcatgcccc ttatgtccag ggcttcacac atgctacaat     1200
ggccggtaca gagggctgcg ataccgtgag gtggagcgaa tcccttaaag ccggtctcag     1260
ttcggatcgg ggtctgcaac tcgacccgt gaagtcggag tcgctagtaa tcgcagatca      1320
gcaacgctgc ggtgaatacg ttcccgggcc ttgtacacac cgcccgtcac gtcatgaaag     1380
tcggtaacac ccgaagccgg tggcctaacc ccttgtggga gggagccgtc gaaggtggga     1440
tcggcgattg ggacgaagtc gtaacaaggt agccgtaccg                           1480
```

RHODOCOCCUS MICROORGANISMS AND PROCESS FOR PRODUCING AMIDE COMPOUNDS

This application is the national phase under 35 U.S.C. §371 of PCT International Application No. PCT/JP99/06994 which has an International filing date of Dec. 13, 1999, which designated the United States of America.

TECHNICAL FIELD

This invention relates to microorganisms useful for providing amides from nitrites and processes for producing amide compounds by using the microorganisms.

BACKGROUND ART

Amides and derivatives thereof are useful compounds that are utilized in various fields. For example, 2-hydroxy-4-butyric acid obtained by hydrolyzing 2-hydroxy-4-methylthiobutyramide is utilized as an additive to feed for supplementing the lack of amino acids containing sulfur in rearing livestock, particularly poultry.

In recent years, processes for producing amides from nitrites by utilizing the action of microorganisms or enzymes extracted from microorganisms are proposed. As the microorganisms, there are presented, for example, microorganisms belonging to the genus Bacillus, the genus Bacteridium, the genus Micrococcus and the genus Brevibacterium (Japanese Patent Publication No. 21519/1987 (JP-B-62-21519)), microorganisms belonging to the genus Corynebacterium and the genus Nocardia (Japanese Patent Publication No. 17918/1981 (JP-B-56-17918)), microorganisms belonging to the genus Pseudomonas (Japanese Patent Publication No. 37951/1984 (JP-B-59-37951)), microorganisms belonging to the genus Rhodococcus, the genus Arthrobacter and the genus Microbacterium (Japanese Patent Application Laid-Open No. 162193/1986 (JP-A-61-162193)), microorganisms belonging to the genus Fusarium (Japanese Patent Application Laid-Open No. 86889/1989 (JP-A-64-86889)), microorganisms belonging to the genus Acinetobacter (Japanese Patent Application Laid-Open No.154692/1990 (JP-A-2-154692)).

Moreover, as the processes for forming amides from nitriles, there are known, for example, a process using a strain of the genus Xanthobacter (Japanese Patent Application Laid-Open No. 154692/1990 (JP-A-2-154692)), a process using a strain of the genus Klebsiella (Arch. Microbiology, Vol. 156, pages 231–238 (1991)), a process using a strain of the genus Streptomyces, the genus Serratia, the genus Erwinia, the genus Tukamurella, the genus Gordona, the genus Morganella, the genus Proteus, the genus Enterobacter, the genus Microascucs, the genus Camdida or the genus Pantoea (Japanese Patent Application Laid-Open No. 15384/1993 (JP-A-5-15384)), a process using a strain of the genus Citrobacter (Japanese Patent Application Laid-Open No. 30983/1993 (JP-A-5-30983)), a process using a strain of the genus Rhizobium (Japanese Patent Application Laid-Open No. 236977/1993 (JP-A-5-236977)), and a process using a strain of the genus Agrobacterium (Japanese Patent Application Laid-Open No. 14786/1994 (JP-A-6-14786)). However, inanyprocess described above, productivity is low and it is difficult to industrially produce an amide with efficiency.

Japanese Patent Application Laid-Open No. 40899/1992 (JP-A-4-40899) discloses, in a process for producing 2-hydroxy-4-methylthiobutyramide from 2-hydroxy-4-methylthiobutanenitrile, the use of a strain of microorganism belonging to the genus Rhodococcus, the genus Coynebacterium, the genus Pseudomonas, the genus Arthrobacter or the genus Alcaligenes. According to the Examples in this literature, there is described that 2-hydroxy-4-methylthiobutyramide can be produced, at the maximum, a molar concentration of 253 mM (concentration: 37.7 g/L, yield: 63%) from 400 mM of 2-hydroxy-4-methylthiobutanenitrile by the reaction, using Rhodococcus rhodochrous ATCC 33278, for 40 hours. In this process, however, the amide-producing rate is as much low as 1 g/L.hr or lower, and it is unable to raise the productivity and economical efficiency.

Further, WO98/32872 discloses the production of 2-hydroxy-4-methylthiobutyramide from 2-hydroxy-4-methylthiobutanenitrile by using strains 52 and 56 wt of the genus Rhodococcus and its detailed production process. In this process, however, the specific activity of the cell (mycobiont) within one hour from the beginning of the reaction is as much low as 100 μmol/min.g-drycell per 1 g of dried cell (mycobiont), therefore unable to raise the productive efficiency and economical efficiency.

Usually, the more complicated the structure of a nitrile becomes, the lower the hydration activity and the conversion efficiency of nitriles to amides of microorganisms are. Thus, it is difficult to produce amides from nitriles having intricate structures with higher efficiency and at a higher rate.

It is, therefore, an object of the present invention to provide a novel microorganism useful in producing an amide from a nitrile, efficiently and at a high production rate, in which the amide corresponds to the nitrile, and a process for producing an amide compound using the microorganism.

It is another object of the present invention to provide a novel microorganism capable of producing an amide from a nitrile at a high production rate, even if the nitrile has a complicated structure, and a process for producing an amide compound using the microorganism.

DISCLOSURE OF INVENTION

The present inventors did much investigation to accomplish the above objects and, as a result, found a novel species of microorganism having an ability to produce an amide compound from a nitrile with high productivity. The present invention has been accomplished based on the above findings.

Thus, the microorganism of the present invention is a novel species of microorganism having a base sequence shown by sequence No.1 or sequence No.2 of the sequence listing as a base sequence of 16S rRNA gene. The microorganism usually has an ability to convert a nitrile to an amide. The microorganism may be a strain of microorganism belonging to the genus Rhodococcus, such as Rhodococcus sp. Cr4 strain (FERM BP-6596) or Rhodococcus sp. Am8 strain (FERM BP-6595). Moreover, the present invention includes a process for producing an amide compound comprising allowing the microorganism or a preparation derived therefrom to act upon a nitrile thereby to convert the nitrile to an amide. The nitrile may be a cyanohydrin such as 2-hydroxy-4-methylthiobutanenitrile.

BEST MODE FOR CARRYING OUT THE INVENTION

Figure 1:
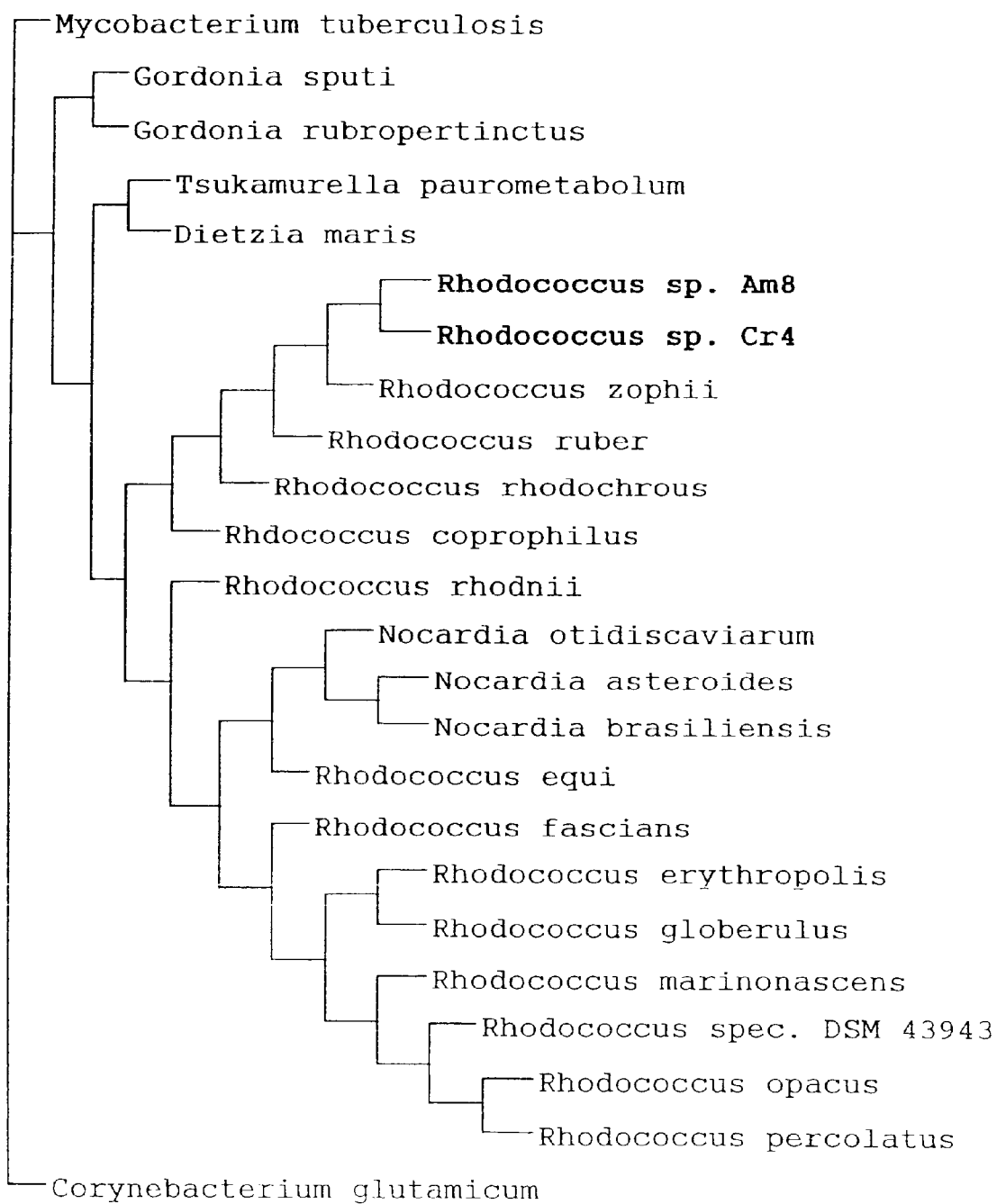
FIG. 1 is a view of a genealogical tree based on the homology, in 16S rRNA gene, of the base sequences of the novel strains of microorganisms of the present invention belonging to the genus Rhodococcus and an affinity strain.

As the strains of microorganisms of the present invention, in so far as they comprise a base sequence designated by the sequence No. 1 or the sequence No. 2 at the sequence listing and have a common function (i.e., the function of producing an amide from a nitrile), use can be made of any type of strain, for example, wild strains, mutants, or recombinants which are derived from strains of microorganisms by means of genetic technologies such as cell fusion or gene manipulation. Moreover, the microorganism of the present invention includes a microorganism having a base sequence substantially equational or equivalent to the base sequence represented by the sequence No. 1 or 2.

Microorganisms having the base sequence mentioned above can be obtained by separating a number of nitrile-decomposing strains from soil. As a strain which has specially high ability to convert nitriles to amides, there may be exemplified Rhodococcus sp. Cr4 strain and Rhodococcus sp. Am8 strain. These microorganisms have been respectively deposited in the National Institute of Bioscience and Human Technology located at 1–3, Higashi 1 chome, Tsukuba-shi, Ibaraki-prefecture 305–8566, Japan, as FERM BP-6596 (deposit day: Dec. 8, 1998) and FERM BP-6595 (deposit day: Dec. 8, 1998). The Rhodococcus sp. Cr4 strain was separated from soil collected from fields located in Okayama-shi, Okayama-prefecture. As the separating process of the strain, an enrichment culture with a selective medium was used [the composition of the $MgSO_4 \cdot 7H_2O$ 0.01 g, a vitamin mixed solution 0.1 ml, $CoCl_2 \cdot 6H_2O$ 0.1 mg, $FeSO_4$ 0.1 mg, distilled water 100 ml, pH 6.0]. The vitamin mixed solution has a composition of, in 1 liter of distilled water, biotin 100 mg, calcium pantothenate 20 mg, inositol 100 mg, nicotinic acid 20 mg, pyridoxine HCl 20 mg, p-aminobenzoic acid 10 mg, riboflavin 10 mg and folic acid 0.5 mg.

Moreover, the Rhodococcus sp. Am8 strain was separated from soil collected from a paddy field located in Gifu-shi, Gifu-prefecture. This strain was separated through enrichment culture using the same medium composition as that in the case with the Cr4 strain.

Both of the strains are aerobic gram-positive bacilli and contain mesodiaminopimelic acid in the cell wall composition. Mycolic acids contained in the strains have carbon compositions of $C_{40-48}$. In accordance with Bergey's manual of determinative bacteriology, ninth edition, 1994, the both strains were found to be microorganisms belonging to the genus Rhodococcus, based on the above mycological properties.

The base sequences of 16S ribosomal RNA (rRNA) genes of both of the strains were determined. Concretely, DNAs were extracted from the both strains, the bases of the 16S rDNA corresponding to the 16S rRNA were amplified by way of a conventional polymerase chain reaction (PCR) method and then the base sequences were determined by a sequencer. The base sequences obtained from the both strains were completely the same. The determined base sequences are shown by the sequence No. 1 and sequence No. 2 in the sequence listing. Further, based on the obtained base sequences, database searches were made thereby to examine the homology between the both strains and their affinity strains. The results are shown in the tables 1 and 2.

TABLE 1

| Strains | 1. | 2. | 3. | 4. | 5. | 6. | 7. | 8. | 9. | 10. | 11. | 12. |
|---|---|---|---|---|---|---|---|---|---|---|---|---|
| 1. Rhodococcus sp. Am8 | — | | | | | | | | | | | |
| 2. Rhodococcus sp. Cr4 | 100.0 | — | | | | | | | | | | |
| 3. Rhodococcus zophii | 99.3 | 99.3 | — | | | | | | | | | |
| 4. Rhodococcus ruber | 98.1 | 98.1 | 97.7 | — | | | | | | | | |
| 5. Rhodococcus rhodochrous | 97.9 | 97.9 | 97.6 | 97.5 | — | | | | | | | |
| 6. Rhodococcus coprophilus | 98.2 | 98.2 | 97.8 | 97.3 | 97.6 | — | | | | | | |
| 7. Rhodococcus rhodnii | 97.1 | 97.1 | 97.0 | 96.7 | 96.3 | 96.0 | — | | | | | |
| 8. Nocardia otidiscaviarum | 95.0 | 95.0 | 95.0 | 94.6 | 94.3 | 94.8 | 95.6 | — | | | | |
| 9. Nocardia asteroides | 94.5 | 94.5 | 94.3 | 94.2 | 94.1 | 94.8 | 94.9 | 97.5 | — | | | |
| 0. Nocardia brasiliensis | 94.7 | 94.7 | 94.8 | 94.7 | 94.6 | 94.2 | 95.5 | 96.7 | 97.9 | — | | |
| 1. Rhodococcus equi | 96.7 | 96.7 | 96.4 | 95.9 | 96.4 | 95.8 | 96.4 | 96.4 | 96.1 | 96.2 | — | |
| 2. Rhodococcus spec. DSM 43943 | 96.4 | 96.4 | 96.1 | 95.3 | 95.5 | 96.4 | 96.3 | 96.0 | 95.8 | 95.2 | 97.3 | — |
| 3. Rhodococcus marinonascens | 96.6 | 96.6 | 96.3 | 95.5 | 95.9 | 97.0 | 96.3 | 95.5 | 96.0 | 95.5 | 97.1 | 99.0 |
| 4. Rhodococcus erythropolis | 96.1 | 96.1 | 95.9 | 95.5 | 95.8 | 96.6 | 96.6 | 95.6 | 95.8 | 95.5 | 96.5 | 98.0 |
| 5. Rhodococcus globerulus | 95.7 | 95.7 | 95.6 | 95.1 | 95.3 | 95.9 | 96.4 | 95.9 | 95.3 | 95.1 | 96.8 | 98.4 |
| 6. Rhodococcus fascians | 95.3 | 95.3 | 95.3 | 95.0 | 95.0 | 95.9 | 96.4 | 95.8 | 95.3 | 94.9 | 96.2 | 97.4 |
| 7. Rhodococcus opacus | 96.7 | 96.7 | 96.5 | 95.7 | 95.9 | 96.3 | 96.4 | 96.1 | 96.1 | 95.7 | 97.8 | 99.0 |
| 8. Rhodococcus percolatus | 96.1 | 96.1 | 95.8 | 95.0 | 95.4 | 95.9 | 95.8 | 95.7 | 95.8 | 95.3 | 97.1 | 98.8 |
| 9. Gordonia sputi | 94.3 | 94.3 | 94.1 | 94.4 | 94.1 | 93.4 | 94.2 | 92.7 | 93.2 | 94.2 | 93.5 | 92.9 |
| 0. Gordonia rubropertinctus | 94.4 | 94.4 | 94.4 | 94.1 | 94.7 | 94.0 | 94.9 | 93.8 | 93.6 | 94.7 | 94.7 | 93.7 |
| 1. Mycobacterium tuberculosis | 92.2 | 92.2 | 92.1 | 92.9 | 92.1 | 92.4 | 92.7 | 92.9 | 92.7 | 91.9 | 92.4 | 92.4 |
| 2. Tsukamurella paurometabolum | 95.4 | 95.4 | 95.3 | 94.9 | 95.1 | 95.0 | 95.6 | 94.3 | 94.7 | 93.9 | 95.2 | 95.4 |
| 3. Dietzia maris | 94.5 | 94.5 | 94.4 | 94.4 | 95.0 | 94.7 | 94.7 | 93.1 | 93.3 | 93.0 | 94.6 | 95.0 |
| 4. Corynebacterium glutamicum | 91.7 | 91.7 | 91.6 | 91.0 | 91.7 | 91.5 | 91.8 | 90.1 | 89.5 | 89.5 | 91.0 | 91.1 |

TABLE 2

| Strains | 13. | 14. | 15. | 16. | 17. | 18. | 19. | 20. | 21. | 22. | 23. |
|---|---|---|---|---|---|---|---|---|---|---|---|
| 1. Rhodococcus sp. Am8 | | | | | | | | | | | |
| 2. Rhodococcus sp. Cr4 | | | | | | | | | | | |
| 3. Rhodococcus zophii | | | | | | | | | | | |
| 4. Rhodococcus ruber | | | | | | | | | | | |
| 5. Rhodococcus rhodochrous | | | | | | | | | | | |
| 6. Rhodococcus coprophilus | | | | | | | | | | | |

TABLE 2-continued

| Strains | 13. | 14. | 15. | 16. | 17. | 18. | 19. | 20. | 21. | 22. | 23. |
|---|---|---|---|---|---|---|---|---|---|---|---|
| 7. *Rhodococcus rhodnii* | | | | | | | | | | | |
| 8. *Nocardia otidiscaviarum* | | | | | | | | | | | |
| 9. *Nocardia asteroides* | | | | | | | | | | | |
| 0. *Nocardia brasiliensis* | | | | | | | | | | | |
| 1. *Rhodococcus equi* | | | | | | | | | | | |
| 2. *Rhodococcus spec.* DSM 43943 | | | | | | | | | | | |
| 3. *Rhodococcus marinonascens* | — | | | | | | | | | | |
| 4. *Rhodococcus erythropolis* | 98.3 | — | | | | | | | | | |
| 5. *Rhodococcus globerulus* | 97.8 | 98.5 | — | | | | | | | | |
| 6. *Rhodococcus fascians* | 97.1 | 97.3 | 97.0 | — | | | | | | | |
| 7. *Rhodococcus opacus* | 98.5 | 97.5 | 97.8 | 96.9 | — | | | | | | |
| 8. *Rhodococcus percolatus* | 98.1 | 97.3 | 97.6 | 96.7 | 99.0 | — | | | | | |
| 9. *Gordonia sputi* | 92.9 | 93.2 | 92.9 | 92.4 | 93.3 | 93.0 | — | | | | |
| 0. *Gordonia rubropertinctus* | 93.6 | 93.6 | 93.7 | 93.7 | 93.9 | 93.6 | 97.0 | — | | | |
| 1. *Mycobacterium tuberculosis* | 92.7 | 92.0 | 92.1 | 92.2 | 92.4 | 92.2 | 91.3 | 91.8 | — | | |
| 2. *Tsukamuralla paurometabolum* | 95.3 | 95.2 | 95.4 | 94.7 | 95.7 | 95.7 | 93.9 | 93.9 | 95.2 | — | |
| 3. *Dietzia maris* | 95.1 | 95.2 | 95.1 | 94.2 | 94.9 | 94.7 | 93.1 | 93.2 | 92.0 | 95.6 | — |
| 4. *Corynebacterium glutamicum* | 90.8 | 90.9 | 90.9 | 91.5 | 91.2 | 90.7 | 89.8 | 90.3 | 89.7 | 91.1 | 91.8 |

Furthermore, the genealogical tree was drawn based on the above results of the homology. The results are shown in FIG. 1. As shown in Tables 1 and 2, the base sequences of the both strains show not more than 99.3% homology relative to other species of the genus Rhodococcus. Thus, the both strains were found to positively be novel microorganisms.

The above microorganisms are useful for producing amide compounds from nitriles.

The nitrites are not particularly restricted and may be selected from a broad range of nitrile compounds. Typical nitrites may be represented by, for example, the formula RCN or RCOCN, wherein R represents an aliphatic hydrocarbon group, an alicyclic hydrocarbon group, an aromatic hydrocarbon group or a heterocyclic group; and such group may have a substituent. Nitriles include polynitriles. That is, the aliphatic hydrocarbon group, the alicyclic hydrocarbon group, the aromatic hydrocarbon group or the heterocyclic group may not be restricted to a monovalent group and may be a polyvalent group of divalent or more.

The aliphatic hydrocarbon group includes, for example, saturated aliphatic hydrocarbon groups such as alkyl groups (e.g., $C_{1-12}$alkyl groups such as methyl, ethyl, propyl, isopropyl, butyl, isobutyl, s-butyl, t-butyl, pentyl, hexyl, octyl and decyl group, preferably $C_{1-6}$alkyl groups) and alkylene groups corresponding to the above alkyl groups (e.g., $C_{1-12}$alkylene groups); and unsaturated aliphatic hydrocarbon groups such as alkenyl groups (e.g., $C_{2-12}$alkenyl groups such as vinyl, allyl, 1-propenyl, isopropenyl and 2-butenyl group), divalent groups corresponding to the above alkenyl groups and alkynyl groups (e.g., $C_{2-12}$alkynyl groups such as ethynyl and 2-propynyl group).

The alicyclic hydrocarbon group includes, for example, saturated alicyclic hydrocarbon groups such as cycloalkyl groups (e.g., $C_{3-10}$cycloalkyl groups such as cyclobutyl, cyclopentyl, cyclohexyl and cyclooctyl group) and cycloalkylene groups corresponding to the above cycloalkyl groups; and unsaturated alicyclic hydrocarbon groups such as cycloalkenyl groups (e.g., $C_{3-10}$cycloalkenyl groups such as cyclopentenyl and cyclohexenyl group) and divalent groups corresponding to the above cycloalkenyl groups.

As the aromatic hydrocarbon group, there may be mentioned, for example, $C_{6-14}$aryl groups such as phenyl and naphthyl group and arylene groups corresponding to the above aryl groups.

The heterocyclic group includes heterocyclic groups each containing at least one hetero atom selected from nitrogen, oxygen and sulfur atoms. The heterocyclic group may be an aromatic heterocyclic (heteroaromatic) group, a nonaromatic heterocyclic group, or a condensed heterocyclic group.

As the hetero ring corresponding to the heterocyclic group, there may be mentioned, for example, a hetero ring containing a nitrogen atom such as pyrroline, pyrrole, piperidine, piperazine, pyridine, pyrimidine, pyridazine, triazole and quinoline; a hetero ring containing an oxygen atom such as tetrahydrofuran, furan and pyran; a hetero ring containing a sulfur atom such as tetrahydrothiophene and thiophene; and a hetero ring having at least two hetero atoms selected from nitrogen atom, oxygen atom and sulfur atom, such as thiazoline, thiadiazoline, thiazole, thiazine and morpholine.

These groups represented by R may, in turn, have a substituent such as halogen atom, hydroxyl group, alkyl group (e.g., $C_{1-5}$alkyl group such as methyl, ethyl, propyl and isopropyl group), aryl group (e.g., $C_{6-14}$aryl group such as phenyl, tolyl, chlorophenyl and naphthyl group), oxo group, alkoxy group (e.g., $C_{1-5}$alkoxy group such as methoxy and ethoxy group), aryloxy group (e.g., phenoxy group), mercapto group, alkylthio group (e.g., $C_{1-5}$alkylthio group such as methylthio and ethylthio group), arylthio group (e.g., $C_{6-14}$arylthio group such as phenylthio group), carboxyl group, ester group (e.g., $C_{1-6}$alkoxy-carbonyl group such as methoxycarbonyl group; and $C_{2-12}$acyloxy group such as acetoxy group), acyl group (e.g., $C_{2-12}$acyl group such as acetyl and benzoyl group), amino group, mono- or di-substituted amino group (e.g. mono- or di-substituted $C_{1-5}$alkylamino group such as methylamino and dimethylamino group) and nitro group. The number of substituents may for example be 1 to about 4.

The aliphatic nitrile includes, for example, saturated or unsaturated aliphatic nitriles having about 2 to 6 carbon atoms (e.g., saturated mononitriles such as acetonitrile, propionitrile, butyronitrile, valeronitrile and isovaleronitrile; saturated dinitriles such as malonitrile and adiponitrile; and unsaturated nitrites such as acrylonitrile, methacrylonitrile, allyl cyanides and crotonitrile). The aliphatic nitrile further includes pyruvonitriles having about 3 to 8 carbon atoms, for example, $C_{1-4}$alkyl-carbonitriles such as acetylnitrile and ethyl-carbonitrile; and $C_{2-5}$alkenyl-carbonitriles such as vinylcarbonitrile and allylcarbonitrile.

The alicyclic nitrile includes, for example, alicyclic nitrites having about 4 to 10 carbon atoms [e.g., saturated alicyclic nitriles such as cyanoC$_{4-8}$cycloalkanes (e.g., cyanocyclopentane and cyanocyclohexane); unsaturated alicyclic nitrites such as cyanoC$_{4-8}$cycloalkene (e.g., cyanocyclopentene and cyanocyclohexene)]. The alicyclic nitrites further includes carbonitriles having about 4 to 12 carbon atoms such as C$_{4-8}$cycloalkanecarbonitriles (e.g., cyclopentanecarbonitrile and cyclohexanecarbonitrile) and C$_{4-8}$cycloalkenecarbonitriles (e.g., cyclopentenecarbonitrile and cyclohexenecarbonitrile).

The aromatic nitrile includes, for example, aromatic C$_{6-14}$mononitriles such as benzonitrile, o-, m- and p-chlorobenzonitrile, o-, m- and p-fluorobenzonitrile, o-, m- and p-nitrobenzonitrile, o-, m- and p-tolubenzonitrile, 2,4-dichlorobenzonitrile, anisonitrile, α-naphthonitrile, β-naphthonitrile, phenylcarbonitrile and naphthylcarbonitrile; and aromatic C$_{6-14}$dinitriles such as phthalonitrile, isophthalonitrile, terephthalonitrile and phthaloyldinitrile. The aromatic nitrile further includes nitriles having a C$_{7-14}$aralkyl group such as phenylacetonitrile, p-hydroxyphenylacetonitrile, p-methoxyphenylacetonitrile, benzylacetonitrile, benzoylacetonitrile, benzylcarbonitrile and phenethylcarbonitrile.

The heterocyclic nitrile includes nitrile compounds having a 5- or 6-membered hetero ring group containing a hetero atom, for example, 5- or 6-membered heterocyclic nitriles containing a sulfur atom as a hetero atom such as 2-thiophenecarbonitrile, cyanothiophenes, cyanothiapyrans and thiapyrancarbonitriles; 5- or 6-membered heterocyclic nitriles containing an oxygen atom as a hetero atom such as cyanofurans, cyanopyrans, furancarbonitriles and pyrancarbonitriles; 5- or 6-membered heterocyclic nitriles containing a nitrogen atom as a hetero atom such as cyanopyridines, cyanopyrazines, cyanopiperidines, nicotinonitrile and isonicotinonitrile; and 5- or 6-membered heterocyclic nitriles containing two or more hetero atoms such as cyanothiazoles, cyanodioxolanes, cyanomorpholines and triazinecarbonitrile. Moreover, the heterocyclic nitrile may be a condensed cyclic nitrile (e.g., 5-cyanoindole, 2-cyanocoumarone, 2-cyanoquinoline and 2-cyanobenzomorpholine) in which an aromatic ring such as benzene ring is condensed to a hetero ring.

As preferred nitrites, there may be exemplified the nitrites having an amino group, a hydroxyl group or the like, as the substituent. Specifically, aminonitriles (e.g., α-aminonitriles such as aminoacetonitrile, α-aminopropiononitrile and α-aminobutyronitrile; and β-aminonitriles such as 3-aminopropiononitrile) and cyanohydrins are preferred.

As the cyanohydrin, there may be exemplified a compound shown by the following formula (1):

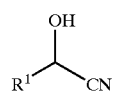

(1)

wherein R$^1$ represents a hydrocarbon group or heterocyclic group, and the group may have a substituent.

As the hydrocarbon group and heterocyclic group represented by R$^1$, and substituents that these groups may have, there may be mentioned those listed in the paragraphs describing R, for example, the aliphatic hydrocarbon groups, alicyclic hydrocarbon groups, aromatic hydrocarbon groups and heterocyclic groups, and the substituents that these groups may have.

Preferred R$^1$ includes, for example, alkyl groups having about 1 to 12 carbon atoms (preferably about 1 to 6 carbon atoms), alkenyl groups having about 2 to 12 carbon atoms, alkynyl groups having about 2 to 12 carbon atoms, cycloalkyl groups having about 3 to 10 carbon atoms, aryl groups having about 6 to 14 carbon atoms and C$_{7-10}$aralkyl groups (e.g., phenylmethyl, 2-phenylethyl, 1-phenylethyl, 3-phenylpropyl and 4-phenylbutyl group), referred in the paragraphs of R.

The carbon number of the cyanohydrin compound may, for example, be 2 to 18, preferably 3 to 12 and more preferably about 3 to 8. The cyanohydrin includes, for example, α-cyanohydrins, β-cyanohydrins and γ-cyanohydrins.

As the α-cyanohydrin, there may be exemplified a compound shown by the following formula (2):

(2)

wherein R$^2$ and R$^3$ may be the same or different from each other and each represents a hydrogen atom or a hydrocarbon group which may have a substituent, and R$^2$ and R$^3$ may bond together with an adjacent carbon atom to form a ring, provided that R$^2$ and R$^3$ are not hydrogen atoms at the same time).

As the hydrocarbon group shown by the R$^2$ or R$^3$ and the substituent that the hydrocarbon group may have, there may be mentioned, for example, the aliphatic hydrocarbon groups, alicyclic hydrocarbon groups and aromatic hydrocarbon groups, and the substituent that the groups may have, referred in the paragraphs of R. Preferred as R$^2$ and R$^3$ are, for example, groups selected from the groups listed above as preferred ones represented by R$^1$.

In the case where R$^2$ and R$^3$ are bond together with an adjacent carbon atom to form a ring, as the ring (ring group), there may be mentioned, for example, cycloalkane ring groups having about 3 to 10 carbon atoms such as cyclobutyl, cyclohexyl, cycloheptyl and cyclooctyl group.

Concrete examples of α-cyanohydrin include saturated aliphatic α-cyanohydrins such as hydroxyacetonitrile, lactonitrile, hydroxymethylthioacetonitrile, acetone cyanohydrin, 2-methylthiolactonitrile, hydroxydimethylthioacetonitrile, 2-hydroxybutyronitrile, 2-hydroxy-4-methylthiobutyronitrile, 2-hydroxy-2-methylbutyronitrile, 2-hydroxy-3-methylbutyronitrile, 2-hydroxy-3-methylthiobutyronitrile, 2-hydroxypentanenitrile, 2-hydroxyhexanenitrile, 2-hydroxy-4-methylthiohexanenitrile and 2-hydroxyoctanenitrile; unsaturated aliphatic α-cyanohydrins such as 2-hydroxy-3-butenenitrile and 2-hydroxy-4-methylthio-3-butenenitrile; alicyclic α-cyanohydrins such as 2-hydroxycyclohexanenitrile, cyclopentanone cyanohydrin and cyclohexanone cyanohydrin; and aromatic α-cyanohydrins such as 1-cyano-1-hydroxybenzene, mandelonitrile, 2-hydroxy-3-phenylbutyronitrile and 2-hydroxy-3-phenyl-4-methylthiobutyronitrile.

As the β-cyanohydrins, there maybe mentioned, for example, 3-hydroxyC$_{3-8}$alkanenitriles such as 3-hydroxypropanenitrile, 3-hydroxy-3-methylthiopropanenitrile, 3-hydroxybutyronitrile, 3-hydroxy-4-methylthionitrile, 3-hydroxyhexanenitrile, 3-hydroxy-4-methylthiohexanenitrile and 3-hydroxy-3-phenylpropanenitrile; 1-cyano-2-hydroxyC$_{3-8}$cycloalkanes such as 1-cyano-2-hydroxycyclopentane and 1-cyano-2- hydroxycyclohexane; 3-hydroxyC$_{3-8}$cycloalkanecarbonitriles such as 3-hydroxycyclopentanecarbonitrile and 3-hydroxycyclohexanecarbonitrile; and aromatic β-cyanohydrins such as o-cyanophenol, 2-cyanonaphthol, 3-hydroxy-3-phenylpropanenitrile, 3-hydroxy-4-phenylbutyronitrile and 3-hydroxy-4-methylthio-4-phenylbutyronitrile.

As the γ-cyanohydrins, there may be mentioned, for example, 4-hydroxyC$_{3-8}$alkanenitriles such as 4-hydroxybutyronitrile, 4-hydroxypentanenitrile and 4-hydroxyhexanenitrile; 3-hydroxyC$_{3-8}$alkanecarbonitriles such as 3-hydroxyhexanecarbonitrile; and aromatic γ-cyanohydrins such as 4-hydroxy-4-phenylbutyronitrile.

The preferred nitrile includes α-cyanohydrins (e.g., aliphatic α-cyanohydrins having about 3 to 8 carbon atoms such as lactonitrile and acetone cyanohydrin), specifically, α-cyanohydrins having a methylthio group (e.g., 2-hydroxy-4-methylthiobutanenitrile).

The nitrites can be produced in a conventional manner. An aliphatic nitrile, for instance, can be produced by reacting an alkyl halide or a dialkyl sulfate with an alkali cyanide such as potassium cyanide. An aromatic nitrile can be typically produced by a process which comprises diazotizing an amine and reacting the resulting diazo compound with copper (I) cyanide.

Among nitrites, α-cyanohydrin in particular can be produced by a process which comprises permitting hydrogen cyanide to act on an aldehyde or ketone or a process which comprises permitting an alkali cyanide such as potassium cyanide to act on an aldehyde or ketone-sodium hydrosulfite adduct. β-cyanohydrins can be produced by reacting epoxides with hydrogen cyanide.

According to the present invention, the cell (mycobiont) of the microorganism or preparation derived therefrom acts on the above-mentioned nitrile to convert the nitrile into the corresponding amide compound. Preferably, the cell of the microorganism is cultured by using liquid culture medium or plate culture medium, collected, treated to prepare the preparation of the cell such as immobilized cells, crude enzymes or immobilized enzymes if necessary, and allowed to act on the nitrile compound.

As the culture medium, use can be made of culture mediums on which the microorganism can usually be nourished, for example, culture mediums containing at least one carbon source selected from sugars (e.g., glucose, fructose, sucrose, dextrinandstarch), alcohols (glycerol, sorbitol and ethanol), organic acids (e.g., fumaric acid, citric acid, acetic acid and propionic acid) and their salts, and hydrocarbons (e.g., paraffins); a nitrogen source such as ammonium sulfate and ammonium nitrate; an inorganic nutrient such as magnesium sulfate, ferric chloride and cobalt chloride; or a metal; or these culture mediums further incorporating a natural organic nitrogen source such as yeast extract and meat extract.

Where necessary, the medium may be further supplemented with factors which promote the growth or multiplication of the microorganism, buffers effective in maintaining the pH of the medium within an optimum range, and factors (inducers or metals) conducive to enhanced productivity of the reaction product amide.

Examples of the inducer include compounds suitable for each microorganism, that is, nitrile compounds such as acetonitrile, isovaleronitrile, isobutyronitrile and benzonitrile; and amide compounds such as acetamide and propionamide.

These inducers and metals can be used singly or in combination. Moreover, the culture medium may be a liquid culture medium, a solid culture medium (e.g., plate culture medium) or the like.

Cultivation of the microorganisms need only be carried out under a condition favoring their growth. For example, the pH value of the culture medium may usually be about pH 2 to 12, preferably about pH 4 to 10 and more preferably about pH 5 to 8. The temperature for cultivation may, for example, be about 5 to 60° C., preferably about 10 to 50° C. and more preferably about 20 to 40° C. Cultivation need only be carried out until the activity of the microorganism is raised up to its maximum, and the cultivation time may, for example, be about 10 hours to 10 days and preferably about 1 to 4 days. Although the microorganism can be grown either aerobically or anaerobically, aerobic culture is preferred.

The cells (mycobionts or strains) can be collected from the cultured microorganisms by way of a conventional method such as centrifugal separation method. The mycobiont may be disrupted (pulverized, milled or broken up) mechanically, for example, by using a homogenizer, or by ultra sonication.

The microorganisms may be used in the form of a raw mycobiont (cell or strain) or preparations derived therefrom. The preparation may have at least the above base sequence. Examples of the preparation include a variety of preparations that can be provided by subjecting the microorganism to various treatments, for example a mechanical treatment (e.g., a preparation disrupted cells), a solvent-treatment (e.g., an acetone-treated preparation), freezing (e.g., freeze-dried cells) and extraction [e.g., cell extracts such as enzymes (crude enzymes or purified enzymes)]. The preparation may be obtained by combinations of the above treatments. The cells (mycobiont or strains) or their preparations can be immobilized by conventional techniques such as polyacrylamide gel immobilization, polysaccharide gel containing sulfur immobilization (carageenan gel immobilization), alginic acid gel immobilization and agar gel immobilization.

The nitriles can be converted into amides by the reaction in a two phase-system composed of water or a buffer containing the obtained cell or preparation therefrom and an organic solvent (a water-insoluble solvent such as n-hexane and ethyl acetate) containing the cell or preparation and a substrate (i.e., a nitrile compound), or the reaction in a single phase-system constituted of a buffer or water-soluble organic solvent (e.g., ethanol) solution of the substrate (the nitrile compound) to which a suspension of water or a buffer containing the cell or preparation is directly added and mixed. The above substrate (nitrile compound) may not be completely dissolved.

The concentration of the microorganism (cell) or the preparation derived therefrom may for example be about 0.01 to 70% by weight, preferably about 0.05 to 30% by weight and more preferably about 0.1 to 10% by weight. The concentration of the substrate may for example be about 0.1 to 80% by weight, preferably about 1 to 60% by weight and more preferably about 5 to 50% by weight.

The reaction temperature need only be a temperature at which the reaction proceeds, for example, about 0 to 60° C., preferably about 5 to 50° C. and more preferably about 10 to 40° C. For example, the temperature of a reaction system to which a water-soluble organic solvent is added may be not higher than 0° C. The pH of the reaction may be about 3 to 12, preferably about 4 to 10 and more preferably about 5 to 8. The reaction time may be, for example, about 1 minute to 100 hours, preferably about 5 minutes to 50 hours and more preferably about 30 minutes to 30 hours.

The nitrile compounds mentioned above represented by the formulae RCN and RCOCN are converted into the corresponding amide compounds shown by the formulae $RCH_2NH_2$ and $RCOCH_2NH_2$ wherein R has the same meanings defined above. For example, the use of 2-hydroxy-4-methylthiobutyronitrile as the nitrile provides 2-hydroxy-4-methylthiobutyramide.

The obtained amide compounds can be separated or purified in a conventional manner. For example, the amide compound as the object compound may be separated by subjecting the reaction solution to separation means such as concentration, ion-exchange, electrodialysis, extraction, crystallization, membrane separation and centrifugation, or eliminating the cells from the reaction solution by centrifugation, membrane separation or the like followed by the separation means mentioned above.

Moreover, from the obtained amide compounds can be provided carboxylic acids. For example, an amide compound such as a 2-hydroxyamide produced in the present invention is hydrolyzed in accordance with the method described in Japanese Patent Application Laid-Open No. 179183/1998 (JP-A-10-179183) or the like, to form a carboxylic acid such as a 2-hydroxycarboxylic acid. Japanese Patent Application Laid-Open No. 179183/1998 (JP-A-10-179183) discloses that microorganism is allowed to act on a nitrile to form a corresponding amide, the amide is hydrolyzed in the presence of a base (e.g., a hydroxide of an alkali metal such as sodium hydroxide) to produce the corresponding carboxylic acid salt, and the carboxylic acid salt is electrodialyzed to produce the corresponding carboxylic acid and base. Combination use of the above method and the process for producing amide compounds by the microorganism of the present invention ensures the production of the carboxylic acid, free from a by-product such as ammonium bisulfate, without using sulfuric acid as a hydration catalyst for nitriles.

INDUSTRIAL APPLICABILITY

The novel microorganisms of the present invention have an excellent ability to convert nitrites to amides and show high reaction activity and selectivity toward the converting reaction, owing to their specific base sequences. Moreover, from nitrile compounds can be formed the corresponding amide compounds at a high production rate even if the structures of the nitrile compounds are complicated. Further, amide compounds can be formed efficiently and with high productivity by allowing the microorganism to act on a nitrile compound.

EXAMPLES

The following examples are intended to describe this invention in further detail and should by no means be interpreted as defining the scope of the invention.

Quantitative determination of the reaction products was conducted by using high performance liquid chromatography [column: J' sphere ODS-M80 (4.6 mm×250 mm, manufactured by YMC, Ltd.) under the following conditions.

Mobile phase: phosphoric acid (0.1 weight % concentration): acetonitrile: methanol=8:1:1

Flow rate: 1.0 mL/minute

Detection wavelength: 210 nm

Column temperature: 40° C.

Example 1

(A) Cultivation

Rhodococcus sp. Cr4 strain and Rhdococcus sp. Am8 strain were cultivated by the following conditions.

(1) Composition of the Culture (% Means Weight/volume %)

| | |
|---|---|
| Crotonamide | 0.5% |
| Yeast extract | 0.2% |
| Peptone | 0.02% |
| Sodium L-glutamate | 1.5% |
| Magnesium sulfate 5 hydrate | 0.05% |
| Cobalt chloride 6 hydrate | $2 \times 10^{-5}\%$ |
| Ferric sulfate 7 hydrate | $2 \times 10^{-5}\%$ |
| Deionized water | the balance |
| pH | 6.8 |

(2) Cultivation Condition

One platinum loop of each cell of Rhodococcus sp. Cr4 strain and Rhodococcus sp. Am8 strain collected from a slant culture medium. The liquid culture medium (50 ml) having the above composition in a Sakaguchi flask was sterilized and inoculated with the cells (strains). The inoculated medium in flask was incubated with shaking at 37° C. for 3 days under aerobic conditions. After completion of incubation, the cells were collected from the liquid culture medium by centrifugation, and there were obtained moist cells.

(B) Reaction

A 50 mL beaker was charged with 0.25 g of the moist cells mentioned above and 23.75 g of 0.05M phosphoric acid buffer (pH 6.0), and the mixture was cooled to 10° C. with stirring. To the mixture, 1.96 g of 2-hydroxy-4-methylthiobutyronitrile was added at the time when the temperature of mixture was 10° C., and reacted for 120 minutes. After the completion of the reaction, 2-hydroxy-4-methylthiobutyronitrile in the reaction mixture was completely consumed in either case of using both strains. Moreover, 2-hydroxy-4-methylthiobutyramide was produced in a concentration of 89.7 g/L in each case, and each yield was almost 100%. Further, the production rate of 2-hydroxy-4-methylthiobutyramide was 45 g/L.hr, and the specific activity per 1 g of dried cell (mycobiont) was 7800 μmol/min.g-drycell.

[Sequence Listing]

[Sequence listing free text]

The sequence No. 1 is the base sequence of 16S rRNA gene of Rhdococcus sp. Cr4 strain (FERM BP-6596).

The sequence No. 2 is the base sequence of 16S rRNA gene of Rhdococcus sp. Am8 strain (FERM BP-6595).

What is claimed is:

1. A biologically pure culture of Rhodococcus sp. strain Am8, FERM BP-6595.

2. A method for producing an amide compound which comprises allowing the microorganism recited in claim 1 or a preparation thereof to act on a nitrile for converting said nitrile into an amide.

3. The method for producing an amide compound according to claim 2, wherein said nitrile is a cyanohydrin shown by the following formula (1):

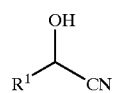
(1)

wherein $R^1$ represents a hydrocarbon group or a heterocyclic group and the group may have a substituent.

4. The method for producing an amide compound according to claim 3, wherein said cyanohydrin is an α-cyanohydrin having a methylthio group.

5. The method for producing an amide compound according to claim 3, wherein said cyanohydrin is 2-hydroxy-4-methylthiobutyronitrile.

6. A biologically pure culture of Rhodococcus sp. strain Cr4, FERM BP-6596.

7. A method for producing an amide compound which comprises allowing the microorganism recited in claim 6 or a preparation thereof to act on a nitrile for converting said nitrile into an amide.

8. The method for producing an amide compound according to claim 7, wherein said nitrile is a cyanohydrin shown by the following formula (1):

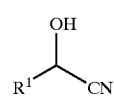
(1)

wherein $R^1$ represents a hydrocarbon group or a heterocyclic group and the group may have a substituent.

9. The method for producing an amide compound according to claim 8, wherein said cyanohydrin is an α-cyanohydrin having a methylthio group.

10. The method for producing an amide compound according to claim 8, wherein said cyanohydrin is 2-hydroxy-4-methylthiobutyronitrile.

* * * * *